United States Patent [19]
Panzera

[11] Patent Number: 4,551,099
[45] Date of Patent: * Nov. 5, 1985

[54] CERAMIC DENTAL RESTORATIVE

[75] Inventor: Carlino Panzera, Belle Mead, N.J.

[73] Assignee: Johnson & Johnson Dental Products Company, East Windsor, N.J.

[*] Notice: The portion of the term of this patent subsequent to Nov. 6, 2001 has been disclaimed.

[21] Appl. No.: 632,100

[22] Filed: Jul. 18, 1984

Related U.S. Application Data

[63] Continuation-in-part of Ser. No. 473,469, Mar. 9, 1983, Pat. No. 4,481,036.

[51] Int. Cl.$^4$ ................................................. C09K 3/00
[52] U.S. Cl. ..................................... 433/212.1; 106/35; 428/689
[58] Field of Search ..................... 501/66, 70; 106/35; 433/208, 209, 199, 202, 201, 212; 428/689

[56] References Cited

U.S. PATENT DOCUMENTS 3,274,006 9/1966 McKinnis ............................... 501/66
3,902,881 9/1975 Pirooz .................................... 501/66

*Primary Examiner*—Lorenzo B. Hayes
*Attorney, Agent, or Firm*—Charles J. Metz

[57] ABSTRACT

An all-ceramic dental restorative comprising a core and a glaze having the following composition:

| Component | Proportion, % |
| --- | --- |
| $SiO_2$ | 71–74 |
| $Al_2O_3$ | 10–12 |
| $K_2O$ | 4–5 |
| $Na_2O$ | 4–5 |
| $CaO$ | 2–4.5 |
| $B_2O_3$ | 3.5–5.5 |

1 Claim, No Drawings

CERAMIC DENTAL RESTORATIVE

This application is a continuation-in-part of copending application Ser. No. 473,469, filed Mar. 9, 1983 now U.S. Pat. No. 4,481,036.

This invention relates to a new family of dental porcelains having lower thermal expansion values than present commercial dental procelains, and are thus useful for use with ceramic copings.

BACKGROUND OF THE INVENTION

Artificial dental crowns and bridges are usually made today using a metallic framework coated with a fused dental porcelain to provide the desired aesthetics. A number of new non-metallic materials are now appearing on the commercial market which are made of mixtures of ceramics, and which are recommended for use in making artificial dental crowns and, in some case, bridges. These materials have coefficients of thermal expansion such lower than existing dental alloys, for instance, $5-8 \times 10^{-6}$ versus $13-14 \times 10^{-6}$, per degree Celsius. Therefore, existing commercially available dental porcelain glazes cannot be used on the non-metallic copings to provide aesthetic properties since the thermal coefficients of expansion are too high.

This invention describes a new family of dental procelains with lower thermal expansion values than commercial dental porcelain glazes, and therefore they match the expansion of the new ceramic copings. The new procelains have the property of being easily modified by minor changes of composition to allow the thermal expansion properties to be changed, in order to match various copings. They also have the desirable property of being stable after repeated firings, in that their coefficients of thermal expansion and color shades remain essentially constant. This is particularly desirable in those cases wherein the glaze will have to be fired more than once. Such instances include those wherein several layers of glaze are used in order to obtain special effects (e.g., a different shade at the tip of the restoration than at the gingival area), and multi-unit bridges. It is another useful property of the glazes of the invention that their maturing temperatures can be modified by minor compositional changes. This is desirable, for instance, in cases wherein several layers of glaze are used so that each successive layer matures at a slightly lower temperature.

SUMMARY OF THE INVENTION

The invention provides an all ceramic dental restoration comprising a ceramic core and a translucent glaze, wherein the glaze has a coefficient of thermal expansion of from about 4 to about $9 \times 10^{-6}$ in./in./°C., a firing temperature of from about 1700° to 1900° F., and which consists essentially of the following components, on a weight basis:

TABLE I

| Component | Proportion, % |
|---|---|
| $SiO_2$ | 71–74 |
| $Al_2O_3$ | 10–12 |
| $K_2O$ | 4–5 |
| $Na_2O$ | 4–5 |
| $CaO$ | 2–4.5 |
| $B_2O_3$ | 3.5–5.5 |

These translucent dental glazes have the desirable property of being stable upon repeated firings at temperatures up to about 1900° F.

DETAILED DESCRIPTION OF THE INVENTION

The translucent glaze composition of this invention can be prepared by melting together sufficient precursor components to yield the composition shown above in the table. Suitable precursors include silica, alumina, boric acid, feldspar, calcium carbonate, sodium carbonate, potassium carbonate, or if desired, the actual oxides, blended in proportion to yield the appropriate ratios shown in the above table.

The preparation of such materials is well known in the art. After the materials are blended, preferably in finely divided powder form such as powder sufficiently fine to pass through a 200 mesh screen (Tyler series), the precursors are heated to a temperature of at least 2100° F., up to 2300° F., and higher, in a crucible to form a glass. The molten glass may then be quenched in water, dried, and ground in a ball mill, to provide the glaze material of the invention in the form of a powder. It is preferred that the powder is ground finely enough so that it will pass through a 160 mesh screen (Tyler series).

The properties of the glaze may be adjusted by applying the following principles:

Within the ranges of component proportions set forth above in Table I, the coefficient of thermal expansion can be increased by decreasing the proportion of $SiO_2$ and/or $B_2O_3$, and/or by increasing the proportion of the alkali metal oxides. The fusion point can be reduced by increasing the proportion of $B_2O_3$, CaO, and/or the alkali metal oxides. As between the two alkali metal oxides, an increase in the $Na_2O:K_2O$ ratio lowers the fusion point. It is well within the skill of the ceramics art to apply these principles to make fine adjustments to the thermal expansion coefficients and fusion temperatures.

Other materials can be employed in the glazes of the invention. For instance, MgO and/or BaO can be used in place of some of the CaO. Some $Li_2O$ can be used in place of some of the $Na_2O$ and/or $K_{2O}$, especially if fusion point reduction is desired. Small amounts of zirconia and zinc oxide can be added to the glaze. And conventional pigments can be added in small amounts (usually less than one weight percent) to tint the glaze. Such pigments include transition metal compounds such as vanadates, manganates, and chromates.

The all ceramic restorations of the invention are made by known techiques. The ceramic core employed can be the material described by Starling et al. in U.S. Pat. No. 4,265,669, Riley et al. in European Patent Application No. 30,850, published on June 24, 1981, and Stephan et al., U.S. Pat. No. 4,374,076. Briefly, the ceramic material used as a core, where fired, comprises a substantially nonporous and shrink-free ceramic body containing a major amount of crystalline material with the remainder being interstitial glass. The crystalline material contains aluminum oxide and magnesium aluminate spinel. It is made from a raw batch containing alumina, magnesia, glass, and a silicone resin binder which decomposes during firing to leave a residue of silica. The alumina and magnesia combine to form spinel during the firing. The spinel expands during its formation to compensate for the shrinkage that would otherwise occur from the formation of the fired ceramic from the raw batch.

One preferred formulation for ceramic core material is the following:

|  | Parts, by Weight |
|---|---|
| Al$_2$O$_3$ | 140 |
| BaO—SiO$_2$—Al$_2$O$_3$ Glass (53% BaO; 42% SiO$_2$; 5% Al$_2$O$_3$) | 30 |
| MgO | 20 |
| Edgar Plastic Kaolin | 9 |
| Calcium Stearate | 2 |
| Acrawax C (Stearyl Amide Wax-mp 290° F.) | 2 |
| Silicone resin (General Electric SR350) | 28 |

The ceramic core may be covered with a layer of translucent body porcelain, if desired, followed by a layer of the glaze of the invention. The layers are applied to the core in the usual manner, as by applying a paste of the porcelain powder in water over the core, shipping to the desired configuration, and then firing. The glaze of the invention is applied in a similar manner.

The following Examples illustrate the invention:

EXAMPLES 1 AND 2

Glazes were made having the compositions set forth below in Table II from silica, tabular grade alumina, potassium carbonate, sodium carbonate, calcium carbonate, and boric acid. The raw materials were blended, ball milled for two hours, and then transferred to a dense alumina crucible. The charge was then fired at 1400° C. and held for 4 hours, quenched in water, crushed, and then ball milled to a powder that passes through a 160 mesh screen (Tyler series).

Thermal expansion test bars were made by pressing 5 grams of powder into a bar $\frac{1}{4} \times \frac{1}{4} \times 2$ inches in dimension, and then firing to the maturing temperature indicated below in Table II. The firing rate was 90° to 100° F. per minute.

The thermal expansion stability of the bars to repeated firings was tested by the following procedure:

The heating cycles were used. Cycle Nos. 1, 4, 7, and 10 were carried out at a 5° C. per minute heat-up rate up to 575° C. The other cycles were carried out at a 90° to 100° F. heat-up rate to the maturing temperature. After these 10 heating cycles, no significant change in the coefficients of thermal expansion of the bars of Examples 1 and 2 was noted.

In order to evaluate the color stability of the glazes, 1½ inch diameter disks were pressed from 7 grams of powder, and were fired under the same conditions as the bars. The disks were then subjected to four heating cycles at a heat-up rate of 90° to 100° F. per minute heat-up rate to the maturing temperature. No color change was noted after these four cycles. (The color was measured by an Applied Color Systems color computer, Model 500).

Table II displays the compositions, maturing temperatures, and the coefficient of thermal expansion for Examples 1 and 2.

TABLE II

|  | Example 1 | Example 2 |
|---|---|---|
| SiO$_2$ | 72.5 | 72.5 |
| Al$_2$O$_3$ | 11.2 | 10.2 |
| K$_2$O | 4.5 | 4.5 |
| Na$_2$O | 4.5 | 4.5 |
| CaO | 2.8 | 3.8 |
| B$_2$O$_3$ | 4.5 | 4.5 |
| Maturing Temp. - °F. | 1825 | 1800 |
| Coeff. of T.E., ($\times 10^6$ in./in./°C.) | 5.3 | 5.5 |

CONTROL EXAMPLES 1–8

In order to investigate the suitability as glazes for use on non-metallic dental copings of several glasses disclosed in the prior art (by McKinnis, U.S. Pat. No. 3,274,006 and Pirooz, U.S. Pat. No. 3,902,881), glasses were made from the formulations listed below in Table III, by the general procedure described above in Examples 1 and 2. The glasses were made in the form of thermal expansion test disks, as described in said Examples. The proportions presented in Table III are on a weight percent basis.

TABLE III

|  | Control No. | | | | | | | |
|---|---|---|---|---|---|---|---|---|
|  | 1 | 2 | 3 | 4 | 5 | 6 | 7 | 8 |
| SiO$_2$ | 75 | 70 | 60 | 55 | 65 | 65 | 65 | 72.2 |
| Al$_2$O$_3$ | 19 | 18 | 6 | 15 | 9 | 15 | 6 | 8.2 |
| K$_2$O | — | 3.5 | 10 | 7 | 10 | 6 | — | — |
| Na$_2$O | — | — | 5 | 6 | 5 | 2 | 5 | 4.6 |
| CaO | 6 | 6 | 16 | 15 | 8 | 6 | 11 | 6.3 |
| B$_2$O$_3$ | — | 2.5 | 3 | 2 | 3 | 2 | 5 | 4.6 |
| MgO | — | — | — | — | — | — | 8 | 4.1 |

The fired and powdered glass was pressed into a disk, and then fired using the heating cycles indicated below. The results obtained were as follows:

Control 1—Heated from 1200° to 1700° F. in a vacuum and from 1700° to 1800° F. in air. (The heating rate for all firing cycles was 100° F. per minute.) Did not fuse or even sinter at all, and therefore is considered to be unsuitable for use as a glaze on a dental porcelain ceramic substrate.

Control 2—Fired from 1200° to 1700° F. in vacuum, and from 1700° to 1800° F. in air. Did not sinter. Another sample fired at 1200° to 1800° F. in vacuum, and from 1800° to 1900° in air. The glass powder sintered, but did not fuse. This glass is not considered to be suitable for use as a glaze on a dental porcelain ceramic substrate.

Control 3—fired at 1200° to 1700° F. in vacuum, and from 1700° to 1800° F. in air. The sample fused, but slumped badly (that is, the glass melted and started to run). The next sample was fired at 1200° to 1600° F. in vacuum and from 1600° to 1700° F., in air. This sample also slumped, but not as much as the previous sample. It also had a gray color. The latter sample (in the form of a bar) was tested for coefficient of thermal expansion, which was found to be $9.25 \times 10^{-6}$ in/in°C. This glass was considered to be not suitable for use as a glaze on a dental ceramic porcelain substrate because it slumped while being fired, the sample that slumped less was gray, and the coefficient of thermal expansion was a little high.

Control 4—First sample fired at 1200° to 1700° F. in vacuum, and then from 1700° to 1800° F., in air. This sample slumped badly and was gray. The next sample was fired at 1200° to 1600° F., in vacuum, and then from 1600° to 1700° F., in air. This sample slumped, but not as badly as the first sample. The coefficient of thermal expansion of this sample (in the form of a bar) was $9.8 \times 10^{-6}$ in/in/°C. Because of the slumping and slightly high coefficient of thermal expansion, this glass was not considered to be suitable for use as a glaze for a dental porcelain ceramic substrate.

Control 5—First sample fired at 1200° to 1700° F. in vacuum, and then from 1700° to 1800° F., in air. It slumped slightly, but was tested (in the form of a bar) for coefficient of thermal expansion, which was found to be $8.5 \times 10^{-6}$ in/in/°C. Another sample was fired at 1200° to 1600° F. in vacuum, and then from 1600° to 1700° F. in air. This sample did not fire completely, i.e., it contained a region of incompletely fused material. This glass was considered not to be suitable for use as a glaze for a dental porcelain ceramic substrate because the sample that did fuse slumped slightly.

Control 6—The first sample was fired at 1200° to 1700° F. In vacuum, and then from 1700° to 1800° F. in air. It sintered, but did not fuse. The next sample was fired from 1200° to 1800° F. in vacuum, and then from 1800° to 1900° F. in air. This sample had only slight fusion. This glass was not considered to be suitable for use as a glaze for a dental porcelain ceramic substrate because it did not fuse at a low enough temperature.

Control 7—This sample was fired at 1200° to 1700° F. in a vacuum, and from 1700° to 1800° F. in air. The coefficient of thermal expansion was $6.6 \times 10^{-6}$ in/in/°C. The appearance of the disk was white opaque, which made it unacceptable for use as a glaze on a dental restoration.

Control 8—Fired from 1200° to 1700° F. in vacuum, and the from 1700° to 1800° F. in air. The coefficient of thermal expansion was $4.9 \times 10^{-6}$ in/in/°C. The appearance of the disk was gray opaque, and was therefore not suitable for use as a glaze on a dental restoration.

What is claimed is:

1. An all-ceramic dental restoration comprising a ceramic core and a translucent glaze, said glaze having a maturing temperature of from about 1700° to about 1900° F., and a coefficient of thermal expansion of from about 4 to about $9 \times 10^{-6}$ in./in./°C., and consisting essentially of, on a weight basis, the following components:

| Component | Proportion, % |
| --- | --- |
| $SiO_2$ | 71–74 |
| $Al_2O_3$ | 10–12 |
| $K_2O$ | 4–5 |
| $Na_2O$ | 4–5 |
| $CaO$ | 2–4.5 |
| $B_2O_3$ | 3.5–5.5. |

* * * * *